United States Patent
Li

(10) Patent No.: US 8,646,453 B2
(45) Date of Patent: Feb. 11, 2014

(54) EXTENDABLE AIRFLOW RESTRICTION SYSTEM

(76) Inventor: Kasey Kai-Chi Li, Palo Alto, CA (US)

( * ) Notice: Subject to any disclaimer, the term of this patent is extended or adjusted under 35 U.S.C. 154(b) by 838 days.

(21) Appl. No.: 12/852,391

(22) Filed: Aug. 6, 2010

(65) Prior Publication Data

US 2010/0326448 A1 Dec. 30, 2010

Related U.S. Application Data

(63) Continuation-in-part of application No. 12/408,605, filed on Mar. 20, 2009.

(51) Int. Cl.
*A61C 5/14* (2006.01)

(52) U.S. Cl.
USPC .......................... 128/848; 128/859; 128/861

(58) Field of Classification Search
USPC .................. 128/848, 859, 861–862, 200.24; 606/151; 600/191, 196, 199, 201, 213
See application file for complete search history.

(56) References Cited

U.S. PATENT DOCUMENTS

| | | | |
|---|---|---|---|
| 4,215,984 A | 8/1980 | Reichley | |
| 4,901,737 A | 2/1990 | Toone | |
| 4,995,404 A | 2/1991 | Nemir | |
| 5,232,362 A | 8/1993 | Kanas | |
| 5,373,859 A | 12/1994 | Forney | |
| 5,464,413 A | 11/1995 | Siska, Jr. et al. | |
| 5,513,986 A | 5/1996 | Feltham et al. | |
| 5,533,470 A | 7/1996 | Rose | |
| 5,915,385 A | 6/1999 | Hakimi | |
| 6,422,243 B1 | 7/2002 | Daram | |
| 6,494,209 B2 | 12/2002 | Kulick | |
| 6,675,804 B1 | 1/2004 | Pivovarov | |
| 6,722,360 B2 | 4/2004 | Doshi | |
| 6,877,513 B2 | 4/2005 | Scarberry et al. | |
| 6,955,172 B2 | 10/2005 | Nelson et al. | |
| 7,073,505 B2 | 7/2006 | Nelson et al. | |
| 7,328,705 B2* | 2/2008 | Abramson | 128/848 |
| 7,334,581 B2 | 2/2008 | Doshi | |
| 7,607,439 B2 | 10/2009 | Li | |
| 7,770,582 B2 | 8/2010 | Chen et al. | |

(Continued)

FOREIGN PATENT DOCUMENTS

| | | |
|---|---|---|
| WO | WO 2009/064914 | 5/2009 |
| WO | WO 2010/107461 | 9/2010 |
| WO | WO 2011/060103 | 5/2011 |

OTHER PUBLICATIONS

Colrain, I.M. et al., "A Pilot Evaluation of a Nasal Expiratory Resistance Device for the Treatment of Obstructive Sleep Apnea," *J Clin Sleep Med*, vol. 4(5): 26 pages, 2008.

(Continued)

*Primary Examiner* — Patricia Bianco
*Assistant Examiner* — Camtu Nguyen
(74) *Attorney, Agent, or Firm* — Levine Bagade Han LLP

(57) ABSTRACT

An extendable airflow restriction system is described herein which may be used to treat various disorders by creating expiratory positive airway pressure while providing for patient comfort regardless of the patient's anatomical variances. Such a device may be removably secured within the patient's mouth and may include an extendable member which may project to urge the patient's upper lip towards the nostrils to restrict airflow. Moreover, the restriction device may include one or more sensors to detect the patient's respiration activity such that the device may be actuated to correspond to the patient's exhalation.

9 Claims, 12 Drawing Sheets

(56) References Cited

U.S. PATENT DOCUMENTS

| | | |
|---|---|---|
| 7,954,494 B1 | 6/2011 | Connor |
| 2001/0047805 A1 | 12/2001 | Scarberry et al. |
| 2002/0144685 A1 | 10/2002 | Ivanovich et al. |
| 2004/0045555 A1 | 3/2004 | Nelson et al. |
| 2004/0045556 A1 | 3/2004 | Nelson et al. |
| 2004/0049102 A1 | 3/2004 | Nelson et al. |
| 2004/0122456 A1 | 6/2004 | Saadat et al. |
| 2004/0194780 A1 | 10/2004 | Doshi |
| 2006/0000472 A1 | 1/2006 | Fenton |
| 2006/0005843 A9 | 1/2006 | Nelson et al. |
| 2006/0032497 A1 | 2/2006 | Doshi |
| 2006/0096600 A1 | 5/2006 | Witt et al. |
| 2006/0144398 A1 | 7/2006 | Doshi et al. |
| 2006/0150978 A1 | 7/2006 | Doshi |
| 2006/0150979 A1 | 7/2006 | Doshi et al. |
| 2007/0277832 A1 | 12/2007 | Doshi et al. |
| 2007/0283962 A1 | 12/2007 | Doshi et al. |
| 2007/0289600 A1 | 12/2007 | Li |
| 2007/0295338 A1 | 12/2007 | Loomas et al. |
| 2008/0041373 A1 | 2/2008 | Doshi et al. |
| 2008/0119885 A1 | 5/2008 | Yazdi |
| 2009/0120446 A1 | 5/2009 | Vaska et al. |
| 2009/0120447 A1 | 5/2009 | Vaska et al. |
| 2009/0123886 A1 | 5/2009 | Vaska |
| 2010/0000551 A1 | 1/2010 | Li |
| 2010/0241159 A1 | 9/2010 | Li |
| 2010/0288288 A1 | 11/2010 | Hegde et al. |
| 2010/0294283 A1 | 11/2010 | Li |
| 2010/0331877 A1 | 12/2010 | Li et al. |
| 2011/0180076 A1 | 7/2011 | Hegde et al. |

OTHER PUBLICATIONS

PCT International Patent Application No. PCT/US2009/069281 filed Dec. 22, 2009 in the name of Li, International Search Report mailed Mar. 11, 2010.

\* cited by examiner

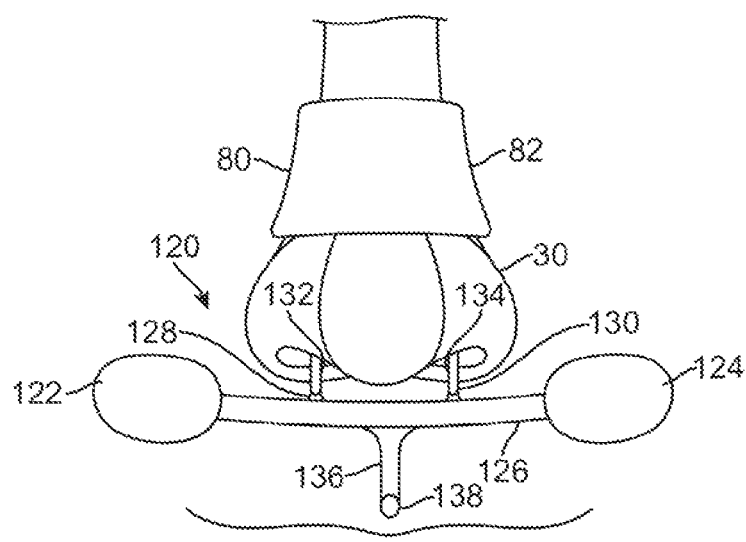
FIG. 8
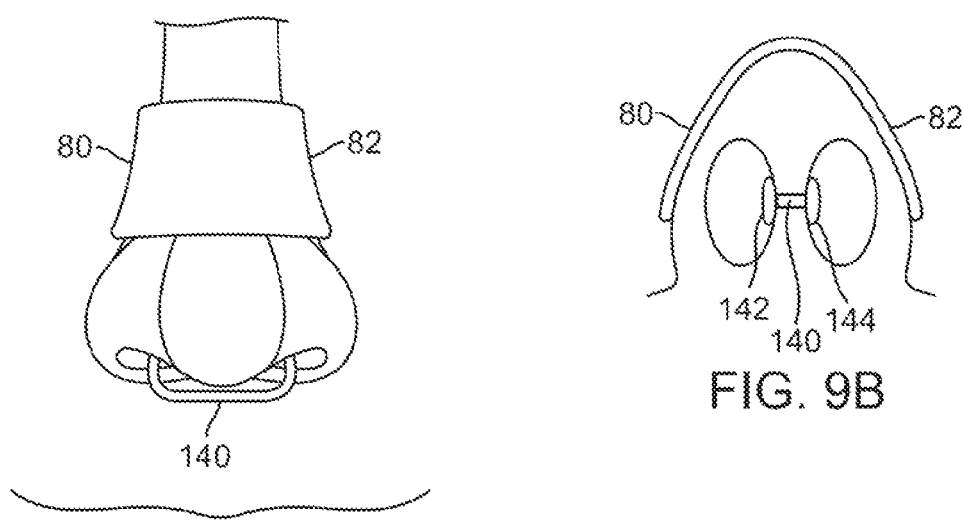
FIG. 9A
FIG. 9B

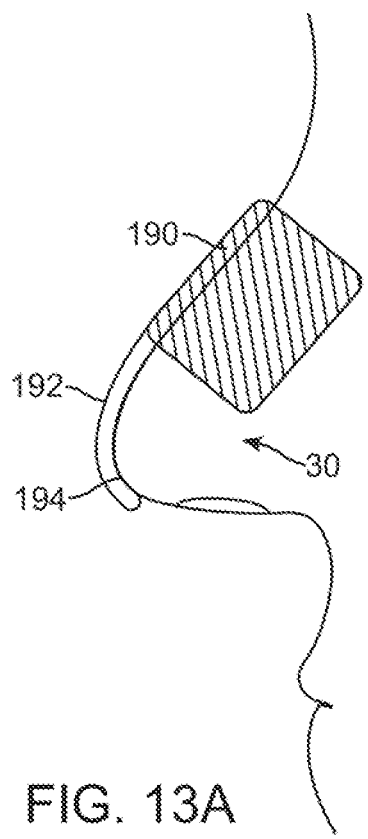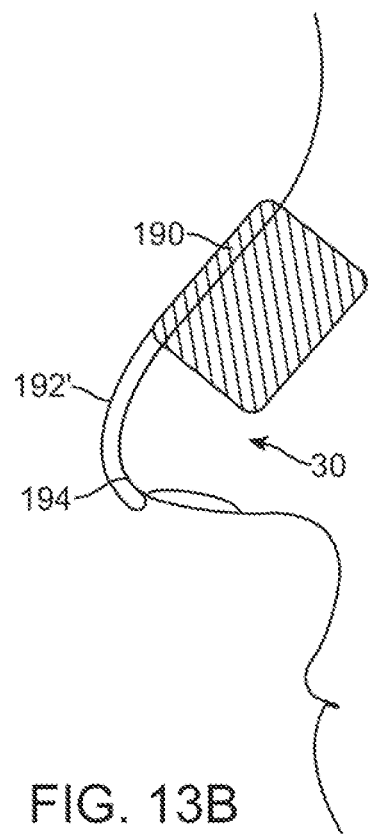

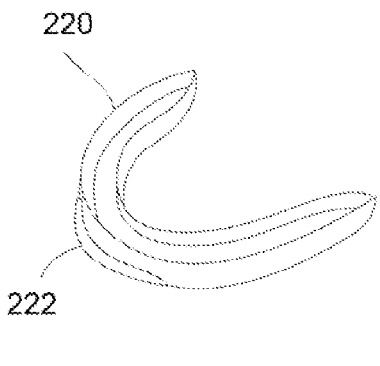
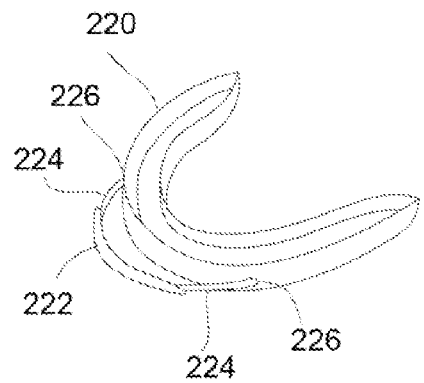
FIG. 15A  FIG. 15B
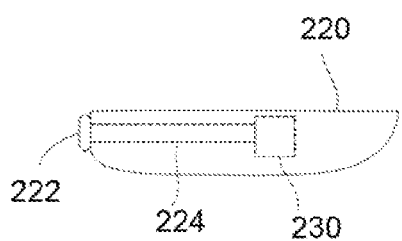
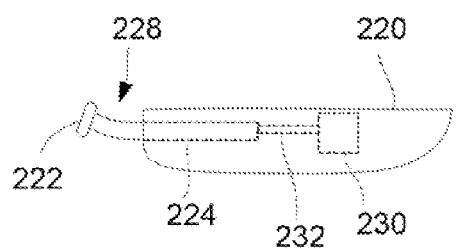
FIG. 16A  FIG. 16B

EXTENDABLE AIRFLOW RESTRICTION SYSTEM

CROSS-REFERENCE TO RELATED APPLICATIONS

This is a continuation-in-part of U.S. patent application Ser. No. 12/408,605 filed Mar. 20, 2009, which is incorporated herein by reference in its entirety.

FIELD OF THE INVENTION

The present invention relates to apparatus and methods for controlling airflow through nasal passages of a patient. More particularly, the present invention relates to methods and apparatus for controllably restricting airflow through the nasal passages of the patient for the treatment of various disorders such as snoring, obstructive sleep apnea (OSA), chronic obstructive pulmonary disease (COPD), asthma, heart failure, etc.

BACKGROUND OF THE INVENTION

In treating various disorders such as snoring, OSA, COPD, asthma, heart failure, etc., therapies such as pulmonary rehabilitation or mechanical ventilation are typically employed. Pulmonary rehabilitation generally involves educating the patient and having them perform various exercises to reduce symptoms and to decreases the disability by helping to condition pulmonary muscles and increase inspiratory tidal volumes. However, such pulmonary rehabilitation exercises require that the patient consciously perform them and they cannot be done while the patient is asleep.

In pulmonary rehabilitation as well as mechanical ventilation devices may aid facilitating the inspiration of air but also provide expiratory resistance in delaying the expiration of air from the patient's lungs. This expiratory delay not only decreases the patient's respiration rate, but the delayed retention of air within the lungs may also facilitate gaseous exchange to improve oxygen saturation levels as well as reduce symptoms of snoring, OSA, COPD, asthma, heart failure, etc.

Treatments such as mechanical ventilation machines are generally utilized to treat respiratory disorders such as OSA. In use, a mask is placed over the patient's nose and/or mouth or nasal pillows are positioned within the nostrils of the patient and air is delivered at a continuous positive pressure into the airways of the patient to prevent or inhibit the upper airways from collapsing during sleep. Such devices, known as continuous positive airway pressure (CPAP) devices may be set a constant pressure level or they may be set at differing pressure levels. However, many patients have difficulties in adjusting to CPAP devices for various reasons.

Yet another treatment involves the placement of airflow resistance devices directly within the nostrils or nasal passages of the patient. These devices are generally removably secured within the nostrils by resistance or within the mouth and incorporate a valve to provide for inspiration of air but provides for increased resistance to expiration to create a positive pressure ventilation. However, such devices requiring securement, e.g., within the nostrils, may be uncomfortable for the user to wear and may also provide a poor fit depending upon the anatomy of the patient's nasal passages.

Accordingly, there is a need for a system which can create expiratory positive airway pressure to treat various conditions while providing for patient comfort regardless of the patient's anatomical variances.

BRIEF SUMMARY OF THE INVENTION

A device which can create expiratory positive airway pressure may be utilized to treat various disorders, e.g., snoring, OSA, COPD, asthma, heart failure, etc., while providing for patient comfort regardless of the patient's anatomical variances. Such a device may be optionally disposable and may be removably secured externally over the patient's nose rather than within the nasal passages to increase patient comfort. The restriction device may be secured, e.g., via an adhesive, to the patient and actuated via any number of mechanical or electromechanical mechanisms. Moreover, the restriction device may include one or more sensors to detect the patient's respiration activity such that the device may be actuated to correspond to the patient's exhalation and squeeze or otherwise constrict the nasal passages at least partially by pressing against the exterior surface of the nose to restrict the expiratory airflow.

One variation of the restriction device may include a first support member and a second support member coupled to one another via an actuatable bridge. The first and second support members may each have a respective contact surface which may each have an adhesive for temporarily securing to the patient's skin surface. Moreover, support members may also comprise various electronic components as well (e.g., a power supply, receiver, processor, etc.) for controlling the actuation of the bridge. When the bridge is actuated, it may bend or constrict to urge or draw the support members towards one another in a first direction. When the bridge is relaxed or reconfigured into a second configuration, the support members may relax or move in a second direction opposite to the first direction where the support members move away from one another back to their initial position.

The actuatable bridge may be comprised of any number of mechanisms to impart the reconfiguration from a relaxed first configuration to a constricting second configuration. For example, the bridge may comprise an electromechanical mechanism such as an electromagnet integrated along the length of the bridge such that passing a current through the bridge magnetizes opposing portions of the bridge to draw and/or repel them towards or away from one another. Alternatively, the bridge may integrate an electroactive polymer strip or portion which reconfigures between a relaxed and constricted configuration when energized to alternate between the configurations described above. Other constricting mechanisms, such as inflation reservoirs may also be utilized.

In use, the restriction device may be placed over a patient's nose when the bridge is relaxed or non-activated. For example, the support members may be securely adhered either directly upon the patient's nose or upon the skin adjacent to the nose on either side such that the bridge is relaxed upon or inferior to the nasal bridge and superior to the nasal openings (nostrils). The bridge may be positioned anywhere along the surface of the nose provided that when bridge reconfigures into its restricted shape, the underlying nasal passages through the nose may become at least partially constricted. With the bridge secured upon the nose by the support members, the bridge may be actuated to constrict, as previously described, such that the underlying nasal passages become restricted anywhere from 1 to 10 mm. Thus, the air to be exhaled through the nasal openings is restricted accordingly and exhalation airflow is reduced to create an expiratory positive airway pressure state in the patient.

Because the nasal passages are desirably constricted upon patient exhalation while remaining unimpeded during inhalation, the restriction device may comprise one or more sensors to detect and distinguish between patient inhalation and exhalation. Such sensors may comprise any number of detection mechanisms, e.g., temperature sensors to detect warm air exhaled from the patient, airflow sensors to detect exhalation activity, etc. The sensors may be electrically coupled to a processor contained, e.g., either in the members or wirelessly to an externally based processor. As the patient inhales air, the restriction device may remain un-activated. However, as the patient exhales, the one or more sensors may detect the exhalation activity and the restriction device may be actuated automatically to constrict the underlying nasal passages until exhalation activity is no longer detected, in which case the device may automatically relax to allow the nasal passages to re-open.

Other variations of the device may include restriction devices incorporated with one or more sensors positioned upon contoured or curved supports as well as support members which may be coupled to one another via a hinge or pivot mechanism. Additional variations may also include systems where a sensing assembly may be unattached to the restriction device but remain in communication, e.g., wirelessly, with one another.

In yet other variations, a portion of the restriction device may be positioned directly within the nasal passages. A nasal clip or attachment may extend across and partially within the nasal openings with extended shutter or flap members extending between the attachments and the central clip or attachment. The shutter or flap members may comprise a movable member which may be rotated or otherwise constricted between a deployed and retracted configuration. In its deployed configuration, exhalation of air may be constricted by the deployed members narrowing the nasal openings. During inhalation, the members maybe reconfigured into a retracted shutter or flap to allow for air to pass relatively unimpeded during inhalation. In this variation, the members may be comprised of a reconfigurable electroactive polymer which may reconfigure itself when a current is applied.

Yet another variation of a restriction device may be positioned directly within the nasal openings where the restriction members may comprise electroactive polymers (e.g., formed into C-shaped, circular, ovular, etc. structures) which expand to reconfigure themselves. In use, each of the restriction members may be positioned within a respective nasal opening such that they present an obstruction to airflow through the openings but when actuated, e.g., during inhalation, they may widen to expand the nasal openings to allow for increased airflow. Another variation may utilize reconfigurable restriction members which extend and contract to alter airflow resistance accordingly.

In yet another variation, the restriction device may be adhered onto the patient's nose. However, rather than the device constricting, it may function to anchor the constricting member which may extend along the nose and around the tip of the nose. For a patient with an otherwise constricted nasal passage, the constricting member (which may be comprised of a reconfigurable electroactive polymer) may be actuated to constrict such that the member may pull on the tip of the nose to increase the airflow through the nasal openings.

In another example, a fluid or gas may be actuated between a reservoir and inflatable respective first and second restriction elements to partially constrict the airflow through the patient's nasal passages. A fluid lumen may connect the reservoir with the restriction elements and the first and/or second actuatable members may be positioned along a surface or within the reservoir such that when the actuatable members are actuated to squeeze or constrict, the fluid contained within the reservoir may be forced or urged out and into the respective first and second inflated restriction members such that inflation of these members constrict the underlying nasal passages to induce the expiratory positive airway pressure. During inhalation, the actuatable members may be relaxed to allow the fluid to flow back from the members into the reservoir. To facilitate the fluid transfer, the members may be made from a distensible material, such as latex, which may be inflated yet is biased to collapse to urge the fluid back into the reservoir.

BRIEF DESCRIPTION OF THE DRAWINGS

FIG. 8 shows a front view of another variation where a restriction device may be positioned along the patient's nose and a separate sensor may be positioned between the nose and mouth of the patient for detecting one or more physiological parameters.

FIGS. 9A and 9B show front and inferior side views, respectively, of another variation where a restriction device may be positioned along the patient's nose and a separate sensor may be positioned along the nasal septum.

FIGS. 13A and 13B show side views of yet another variation where an actuating element may be configured to engage and retract the tip of the nose to facilitate or constrict airflow.

FIGS. 15A and 15B show perspective views of yet another variation having an extendable member which may be projected from an oral appliance for urging the patient's upper lip towards the nostrils.

FIGS. 16A and 16B show corresponding side views of the device of FIGS. 15A and 15B illustrating the movement of the extendable member.

DETAILED DESCRIPTION OF THE INVENTION

In treating various disorders, e.g., snoring, OSA, COPD, asthma, heart failure, etc., a device which can create expiratory positive airway pressure may be utilized which provides for patient comfort regardless of the patient's anatomical variances. Generally, such a device may be optionally disposable and may be removably secured externally over the patient's nose rather than within the nasal passages to increase patient comfort. The restriction device may be secured, e.g., via an adhesive, to the patient and actuated via any number of mechanical or electromechanical mechanisms. Moreover, the restriction device may include one or more sensors to detect the patient's respiration activity such that the device may be actuated to correspond to the patient's exhalation and squeeze or otherwise constrict the nasal passages at least partially by pressing against the exterior surface of the nose to restrict the expiratory airflow.

Figure 1A:
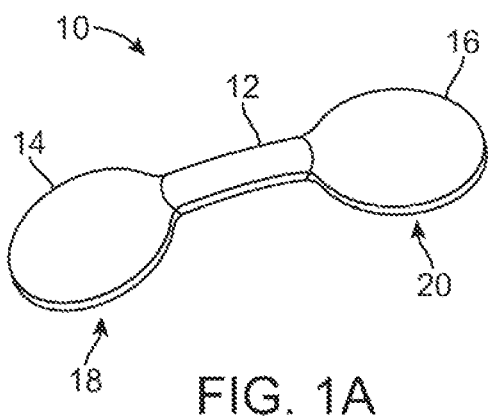
FIGS. 1A to 1C show perspective and respective side views of one variation of an airflow restriction device which may be actuated to constrict a patient's airflow through their nasal passages.

As shown in the perspective view of FIG. 1A, one variation of restriction device 10 is illustrated where a first support member 14 and a second support member 16 may be coupled to one another via an actuatable bridge 12. First and second support members 14, 16 may each have a respective contact surface 18, 20 which may each have an adhesive for temporarily securing to the patient's skin surface. Moreover, support members 14, 16 may also comprise various electronic components as well (e.g., a power supply, receiver, processor, etc.) for controlling the actuation of bridge 12.

Figure 1B:
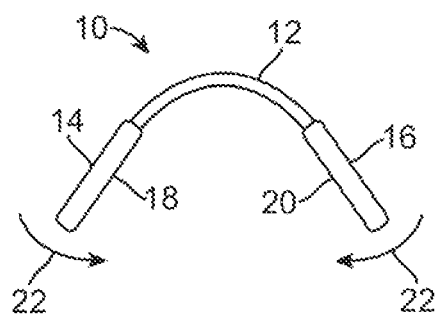
Figure 1C:
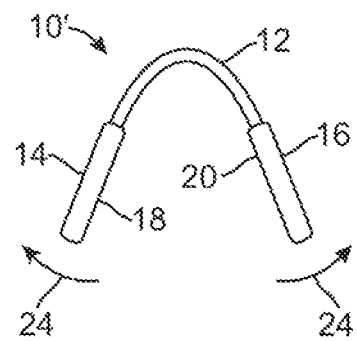

FIGS. 1B and 1C illustrate side views of restriction device 10 in a relaxed configuration and a constricted configuration, respectively. When bridge 12 is in a relaxed or first configuration, support members 14, 16 may rest upon the patient's nose with bridge 12 taking a curved or arcuate shape. When bridge 12 is actuated, bridge 12 may bend or constrict to urge or draw support members 14, 16 towards one another in a first direction 22, as shown by the constricted device 10' in FIG. 1B. When bridge 12 is relaxed or reconfigured into a second configuration, support members 14, 16 may relax or move in a second direction 24 opposite to the first direction where support members 14, 16 move away from one another back to their initial position, as shown in FIG. 1C.

Actuatable bridge 12 may be comprised of any number of mechanisms to impart the reconfiguration from a relaxed first configuration to a constricting second configuration. For example, bridge 12 may comprise an electromechanical mechanism such as an electromagnet integrated along the length of bridge 12 such that passing a current through bridge 12 magnetizes opposing portions of bridge 12 to draw and/or repel them towards or away from one another. Alternatively, bridge 12 may integrate an electroactive polymer strip or portion which reconfigures between a relaxed and constricted configuration when energized to alternate between the configurations described above. Other constricting mechanisms, such as inflation reservoirs may also be utilized, as described in further detail below.

Figure 2A:
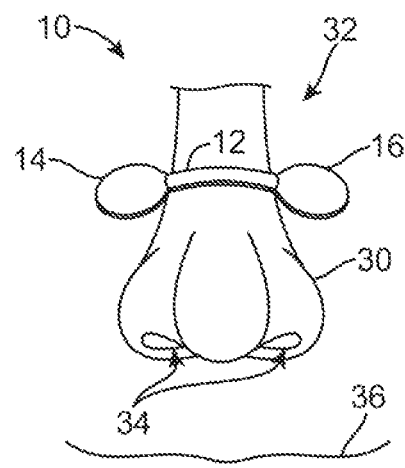
FIGS. 2A and 2B show an example of a device adhered over a patient's nose, e.g., inferior to the bridge of the nose, such that actuation of the device partially constricts the nasal passages to at least partially restrict the airflow during exhalation.

In use, restriction device 10 may be placed over a patient's nose 30 when bridge 12 is relaxed or non-activated. For example, support members 14, 16 may be securely adhered either directly upon the patient's nose 30 or upon the skin adjacent to the nose 30 on either side, as shown in FIG. 2A, such that bridge 12 is relaxed upon or inferior to the nasal bridge 32 and superior to nasal openings (nostrils) 34. In other variations described herein, bridge 12 may also be utilized with other components positioned superior to mouth 36. Bridge 12 may be positioned anywhere along the surface of the nose 30 provided that when bridge 12 reconfigures into its restricted shape, the underlying nasal passages through nose 30 may become at least partially constricted.

Figure 2B:
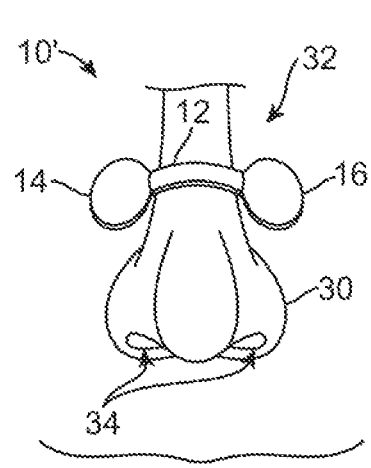

With bridge 12 secured upon nose 30 by support members 14, 16, bridge 12 may be actuated to constrict, as previously described, such that the underlying nasal passages become restricted by bridge 12 and/or members 14, 16 anywhere from 1 to 10 mm. Thus, the air to be exhaled through nasal openings 34 is restricted accordingly and exhalation airflow is reduced to create an expiratory positive airway pressure state in the patient, as shown in FIG. 2B.

Figure 2C:
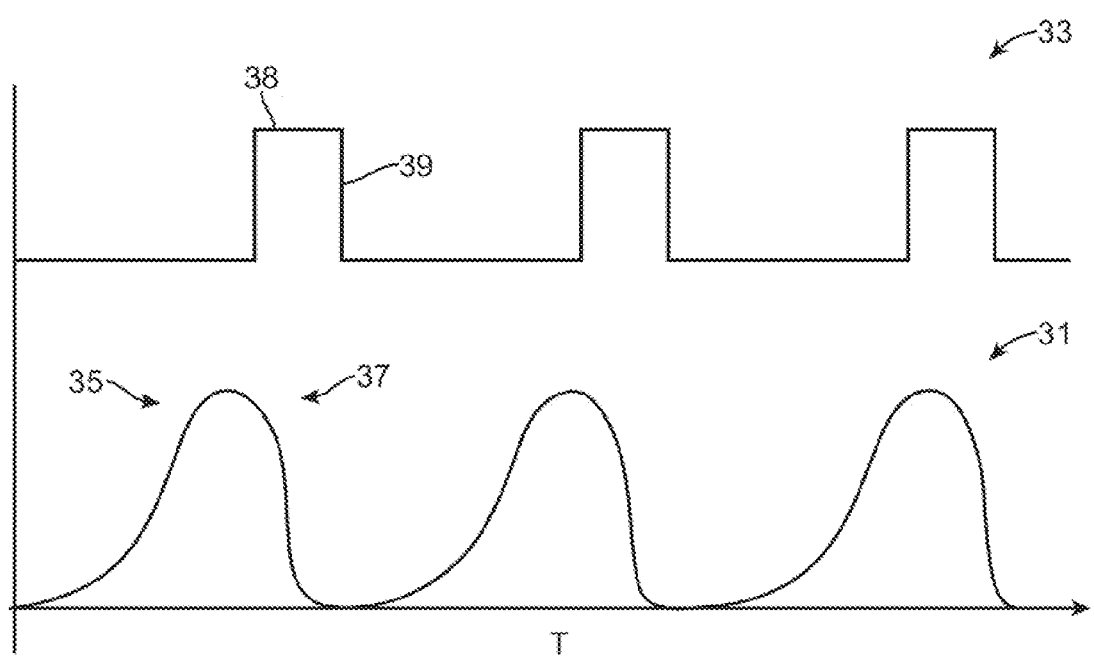
FIG. 2C illustrates a chart of a patient's respiration activity and the corresponding actuation of the restriction device to create expiratory positive airway pressure.

Because the nasal passages are desirably constricted upon patient exhalation while remaining unimpeded during inhalation, restriction device 10 may comprise one or more sensors to detect and distinguish between patient inhalation and exhalation. Such sensors may comprise any number of detection mechanisms, e.g., temperature sensors to detect warm air exhaled from the patient, airflow sensors to detect exhalation activity, etc. The sensors may be electrically coupled to a processor contained, e.g., either in member 14 or 16 or wirelessly to an externally based processor. As shown in the chart of FIG. 2C, a patient's exemplary respiration activity 31 is illustrated indicating inhalation 35 and exhalation 37 over a time period, T, and the corresponding restriction device actuation 33 is illustrated above. As the patient inhales air 35, the restriction device 10 may remain un-activated. However, as the patient exhales 37, the one or more sensors may detect the exhalation activity and restriction device 10 may be actuated 38 automatically to constrict the underlying nasal passages until exhalation activity 37 is no longer detected, in which case device 10 may automatically relax 39 to allow the nasal passages to re-open.

This process of constriction and relaxation may be repeated until the patient de-actives the device 10. Alternatively, device 10 may be optionally programmed to activate after a preset time period and/or to de-activate automatically as well. Moreover, device 10 may be programmed to constrict bridge 12 in a stepped manner over a predetermined time period. For example, bridge 12 may be programmed to constrict 0 mm for the first 15 minutes after activation and then constrict 1 mm for the subsequent 15 minutes and then constrict more than 1 mm for another subsequent time period, etc. Additionally, because the device may be used when the patient is either awake or asleep, device 10 may be programmed to have a fail-safe feature where the device 10 automatically relaxes or releases in the event of any failures such that the nasal passages remain un-constricted until the patient is able to remove the device 10.

Figure 3:
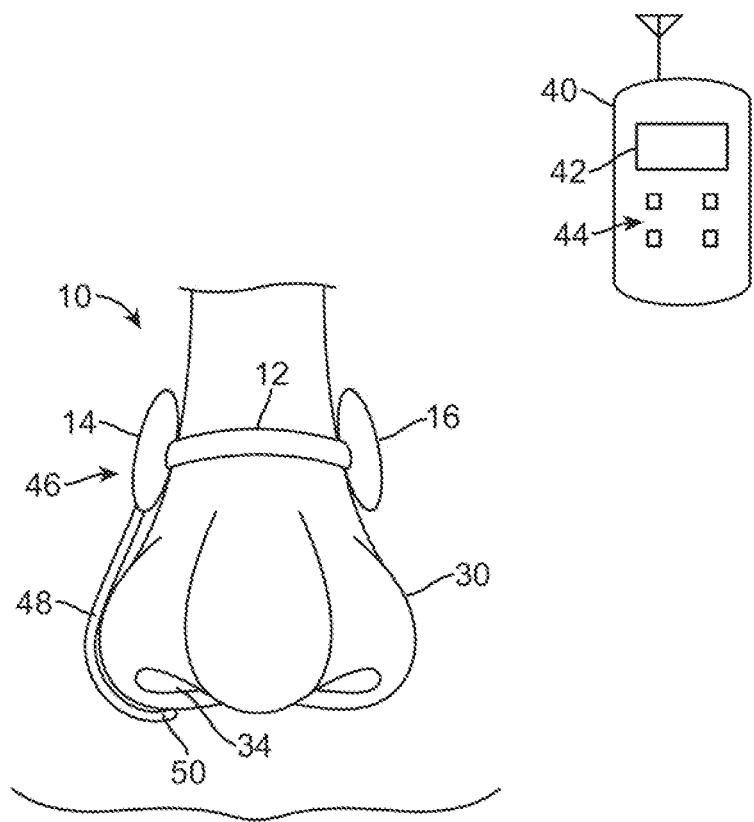
FIG. 3 shows an example of a variation where the device may incorporate a sensor to detect inhalation and exhalation of the patient as well as a controller to control various aspects of the device.

The one or more sensors may be incorporated with device 10 in various configurations. As shown in FIG. 3, a wire or conformable member 48 may extend from support member 14 and/or 16 to a location where sensor 50, which is positioned on a distal end of member 48, may be located proximate to nasal opening 34 to detect the airflow, temperature, or other physiological parameter of the patient. Also shown is an optional controller 40 which may be in wireless (or wired) communications with an electronics assembly 46 via a receiver or transmitter optionally integrated within support member 14 and/or 16. Controller 40 may be configured in a variety of ways and may include a display 42 for indicating any number of parameters or information as well as control pad 44 for providing user input. Alternatively, controller 40 may be integrated with any number of other devices, e.g., PDA, cell phone, watch, etc.

Figure 4A:
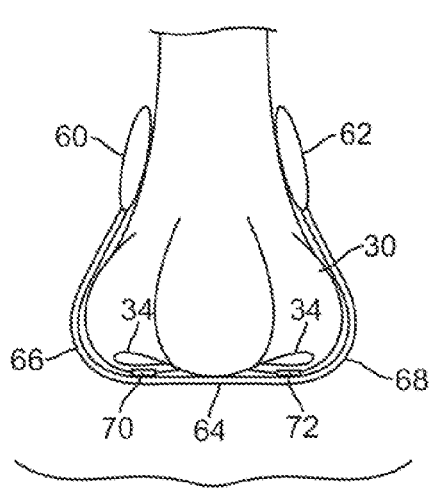
FIGS. 4A and 4B show front and side views, respectively, of another variation of the device positioned upon a patient's nose with one or more sensors in proximity to the nasal passages.
Figure 4B:
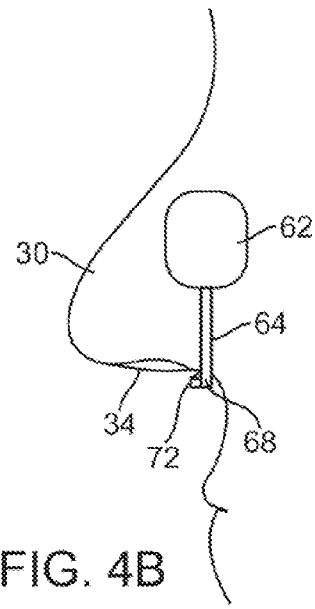

Another variation of the device is shown in the front and side views of FIGS. 4A and 4B, respectively. As illustrated, first support 60 and second support 62 may be secured on either side of nose 30 while actuating bridge 64 may extend and rest along the inferior contour of nose 30 posterior to the nasal openings 34 and superior to the mouth 36 of the patient. Actuating bridge 64 may be accordingly contoured or curved 66, 68 and one or more sensors 70, 72 may be positioned along bridge 64 adjacent to the nasal openings 34 for detecting exhalation activity. In this manner, bridge 64 may be actuated to urge or draw apposed supports 60, 62 towards one another accordingly.

Figure 5A:
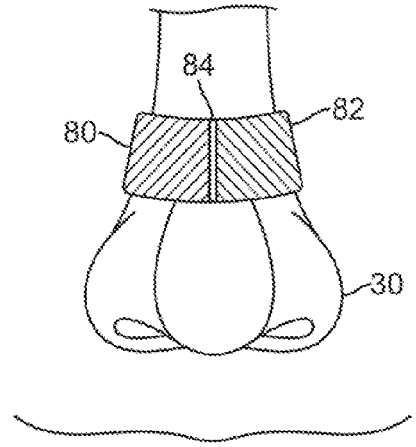
FIGS. 5A and 5B show front and side views, respectively, of yet another variation of the device which may flex or articulate via a hinge or pivot.
Figure 5B:
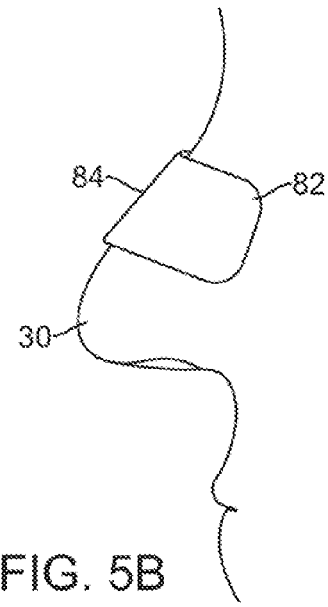

FIGS. 5A and 5B show front and side views, respectively, of another variation of the device where first support 80 and second support 82 are integrated and joined to one another via a hinge or pivot 84 mechanism to form a continuous structure. In this manner, supports 80, 82 may be adhered or fitted onto the patient's nose 30 like a clip mechanism while supports 80, 82 may be secured to nose 30 via an adhesive to via a clamping force. Hinge or pivot 84 may be comprised of an actuating mechanism, as described above, to urge or draw supports 80, 82 towards one another or a separate actuating mechanism may be placed over or upon supports 80, 82 to provide the biasing force to effect constriction.

Figure 6:
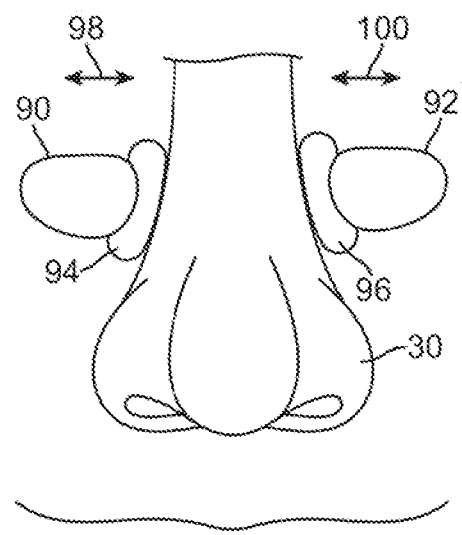
FIG. 6 shows a front view of yet another variation where one or more components may be positioned in apposition against one or both sides of the patient's nose to at least partially constrict airflow.

FIG. 6 shows a front view of yet another variation where first support 90 and second support 92 may be secured along either side of nose 30 such that the supports 90, 92 are unattached to one another. First support 90 may comprise a first actuator 94 in contact against a first surface of the nose 30 while second support 92 may comprise a second actuator 96 in contact against a second surface of the nose 30 opposite to the first surface. One or both actuators 94, 96 may be activated to press against the respective surface of the nose 30 as indicated by the direction of constriction 98 and 100, respectively. Because the supports and actuators are unattached to one another, actuators 94, 96 may be in wireless communication with one another or with an external controller to coordinate their movement. Alternatively, a single support and actuator may be utilized against a single corresponding nasal passage, if so desired.

Figure 7A:
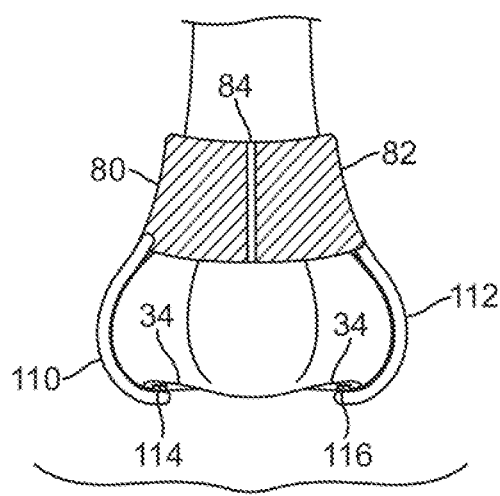
FIGS. 7A and 7B show front and inferior side views, respectively, of yet another variation having one or more sensors which may be positioned directly within a respective nostril.
Figure 7B:
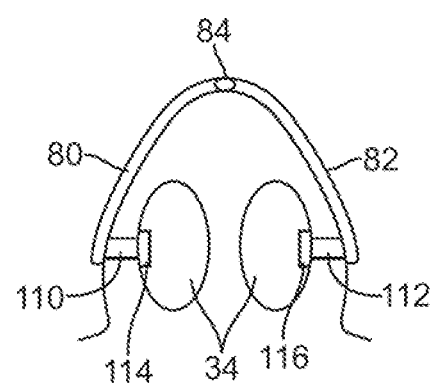

FIGS. 7A and 7B show front and inferior views, respectively, of yet another variation where the device previously described above having first support 80 and second support 82 may further include a first member 110 extending from first support 80 and a second member 112 extending from second support 82. Each support may include a respective first sensor 114 and second sensor 116 which may extend proximate to or partially within the nasal openings 34 for providing respiratory sensing to the device.

Yet another variation is shown in the front view of FIG. 8, which illustrates a restriction device positioned upon the nose 30 and a separate sensing assembly 120 which may be unattached to the restriction device. Any of the restriction device variations shown herein may be utilized with the sensing assembly 120 as practicable, if so desired. As above, sensing assembly 120 may remain in communication, e.g., wirelessly, with the device and/or with an external controller. In either case, this example illustrates a sensing assembly 120 having a first support 122 and a second support 124 with a connecting member 126 extending therebetween. Supports 122, 124 may be temporarily adhered to the skin surface such that connecting member 126 extends between the patient's nose 30 and mouth. A first member 128 having a first sensor 132 may be extend proximate to or partially within a first nasal passage and an optional second member 130 having a second sensor 134 may also extend proximate to or partially within a second nasal passage. Additionally, an optional third member 136 having a third sensor 138 may extend towards the mouth of the patient to detect respiration or other physiological parameters from the patient's mouth.

FIGS. 9A and 9B show another variation in front and inferior views where the restriction device may be positioned upon or over the patient's nose 30, as previously described, along with a separate and unattached connecting member 140. In this variation, connecting member 140 may have a first sensor 142 and an optional second sensor 144 each positioned proximate to or partially within a respective nasal opening. Connecting member 140 may be clipped to the nasal septum to secure it in place or otherwise adhered.

Figure 10A:
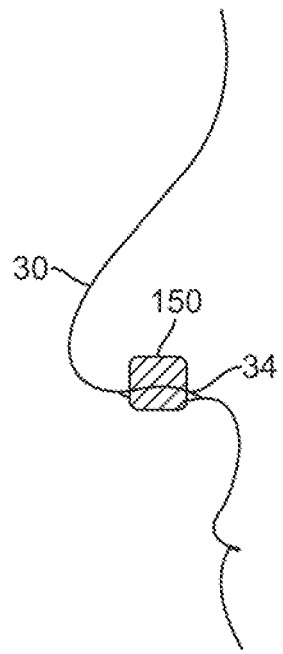
FIG. 10A shows a side view of yet another variation where airflow-restrictive elements may be positioned proximate to the nasal passages.
Figure 10B:
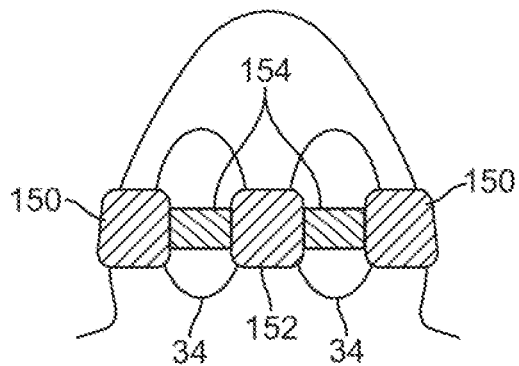
FIGS. 10B and 10C show inferior views of the airflow-restrictive elements actuated between a restrictive and a non-restriction configuration, respectively.
Figure 10C:
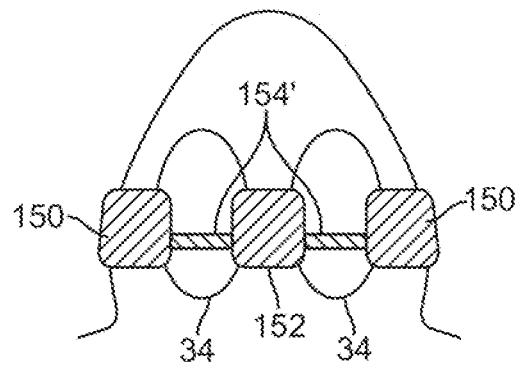

In yet other variations, a portion of the restriction device may be positioned directly within the nasal passages. As shown in the side and inferior views of FIGS. 10A to 10C, nasal clip or attachment 150 may extend across and partially within the nasal openings 34 with extended shutter or flap members 154 extending between attachments 150 and central clip or attachment 152. Shutter or flap members 154 may comprise a movable member which may be rotated or otherwise constricted between a deployed and retracted configuration. In its deployed configuration, shown in FIG. 10B, exhalation of air may be constricted by the deployed members 154 narrowing the nasal openings 34. During inhalation, the members 154 maybe reconfigured into a retracted shutter or flap 154', as shown in FIG. 10C, to allow for air to pass relatively unimpeded during inhalation. In this variation, members 154 may be comprised of a reconfigurable electroactive polymer which may reconfigure itself when a current is applied.

Figure 11A:
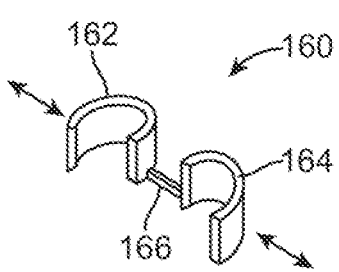
FIGS. 11A and 11B show perspective and inferior views, respectively, of yet another variation where the restrictive device may be positioned within the nasal passages and functions to expand or contract the nasal openings.
Figure 11B:
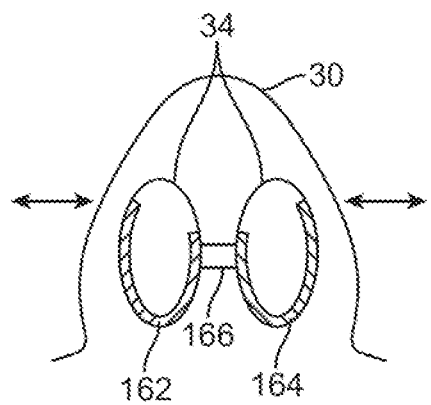

FIGS. 11A and 11B show perspective and inferior views, respectively, of yet another variation of a restriction device 160 which may be positioned directly within the nasal openings 34. Device 160 may comprise a first restriction member 162 and a second restriction member 164 coupled to one another via a connecting bridge 166. Restriction members 162, 164 may comprise electroactive polymers (e.g., formed into C-shaped, circular, ovular, etc. structures) which expand to reconfigure themselves, as indicated in FIG. 11A. In use, each of the restriction members 162, 164 may be positioned within a respective nasal opening 34 with bridge 166 extending therebetween. With the restriction members 162, 164 positioned accordingly, they may present an obstruction to airflow through the openings 34 but when actuated, e.g., during inhalation, they may widen to expand the nasal openings 34 to allow for increased airflow, as indicated in FIG. 11B.

Figure 12A:
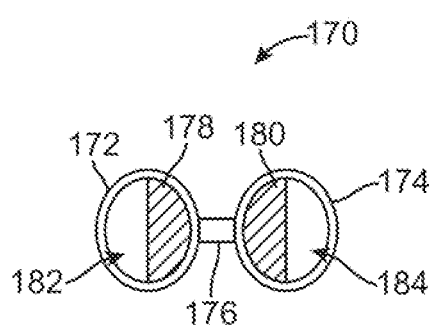
FIGS. 12A and 12B show side views of another variation where one or more restrictive elements may be actuated between a partially closed and opened configuration, respectively.
Figure 12B:
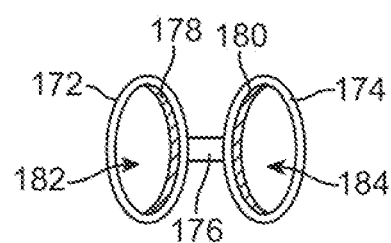

FIGS. 12A and 12B show yet another variation of an example in which restriction device 170 may be formed (e.g., C-shaped, circular, ovular, etc. structures) having a first restriction member 172 and a second restriction member 174 coupled to one another via a connecting bridge 176. Each of the restriction members 172, 174 may define a corresponding first and second airway 182, 184 therethrough with each having a respective first and second reconfigurable obstruction 178, 180 positioned within. During exhalation, obstructions 178, 180 may be deployed to restrict the respective airways, as shown in FIG. 12A. During inhalation, the obstructions 178, 180 may be urged, activated, or otherwise actuated to reconfigure into a low-profile shape such that the airways 182, 184 are relatively unimpeded, as shown in FIG. 12B. Actuation of the obstructions 178, 180 may be done automatically, as previously described.

In yet another variation, FIGS. 13A and 13B show side view of restriction device 190 which may be adhered onto the patient's nose, as above. However, rather than device 190 constricting, it may function to anchor constricting member 192 which may extend along the nose and around the tip 194 of nose 30, as shown in FIG. 13A. For a patient with an otherwise constricted nasal passage, constricting member 192 (which may be comprised of a reconfigurable electroactive polymer) may be actuated to constrict such that member 192' may pull on the tip 194 of nose 30 to increase the airflow through the nasal openings 34.

Figure 14A:
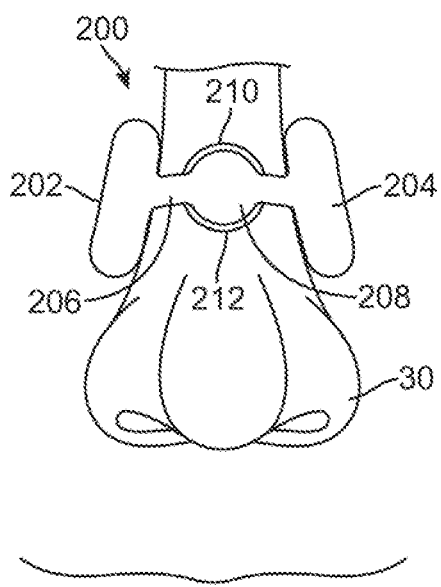
FIGS. 14A and 14B show front views of yet another variation where a fluid or gas may be actuated between a reservoir and respective restriction elements to partially constrict the airflow through the patient's nasal passages.
Figure 14B:
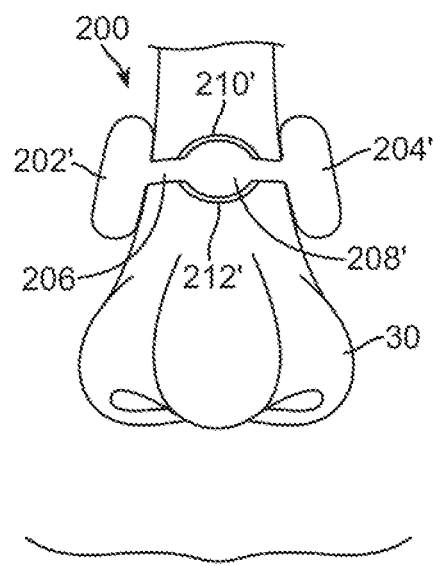

In another example, FIGS. 14A and 14B show restriction device 200 which utilizes a fluid or gas actuated between a reservoir 208 and inflatable respective first and second restriction elements 202, 204 to partially constrict the airflow through the patient's nasal passages. As shown in FIG. 14A, a fluid or gas reservoir 210 may be positioned along the bridging member coupling the inflatable restriction elements 202, 204. A fluid lumen 206 may connect the reservoir 210 with the restriction elements 202, 204 and first and/or second actuatable members 210, 212 may be positioned along a surface or within reservoir 208 such that when actuatable members 210', 212' are actuated to squeeze or constrict, the fluid contained within reservoir 208' may be forced or urged out and into the respective first and second inflated restriction members 202', 204', as shown in FIG. 14B, such that inflation of these members 202', 204' constrict the underlying nasal passages to induce the expiratory positive airway pressure. During inhalation, actuatable members 210, 212 may be relaxed to allow the fluid to flow back from the members 210, 212 into reservoir 208. To facilitate the fluid transfer, members 210, 212 may be made from a distensible material, such as latex, which may be inflated yet is biased to collapse to urge the fluid back into reservoir 208.

In yet another example, rather than restricting the nasal passages by compressing upon the exterior surface of the nose, the upper lip of the patient may be drawn towards the nostril to achieve the desired airflow restriction. As shown in the perspective views of FIGS. 15A and 15B, an example of an oral appliance 220 having an extendable member 222 positioned along an anterior portion of the appliance 220 is illustrated. The appliance 220 may be placed upon the dentition or upper ridge of the patient's mouth when in use with the extendable member 222 initially positioned against the oral appliance 220 in a low profile such that the member 222 rests comfortably within the mouth behind the upper lip.

When actuated, either manually or automatically as described herein, extendable member 222, which may be fabricated from a polymeric or plastic material to have a non-atraumatic surface, may be projected distally to extend from the oral appliance 220 by, e.g., one or more supports 224 which may extend from the appliance 220 through corresponding openings 226. As shown in the side views of FIGS. 16A and 16B, which correspond to the FIGS. 15A and 15B, the member 222 may rest against the oral appliance 220 but may then extend distally when actuated. The extendable member 222 may be supported by one or more supports 224 which may be slidably positioned within the appliance 220 and actuated by one or more corresponding actuators (e.g., motors) contained within assembly 230 contained within or along the appliance 220. The assembly 230 may also optionally incorporate a processor for controlling actuation of the motors. When actuated, the one or more motors may project the supports 224 distally via connectors 232. Additionally, the one or more supports 224 (fabricated from a biocompatible metal, alloy, polymer or plastic) may be configured to have curved or arcuate section 228 which bends in a gentle radius when projected from the oral appliance 220 and free from any constraints to urge the extendable member 222 in a curved trajectory. This feature may be optionally incorporated to facilitate the positioning of the user's upper lip against the nostrils.

Optionally, a covering or distensible membrane may surround the supports 224 such that the gap between the member 222 and oral appliance 220 remains covered and presents a smooth surface to the tissue surfaces within the mouth to prevent or inhibit any potential pinching or trauma to the tissue.

The distance by which the member 222 may project from the appliance 220 may vary anywhere from just a few millimeters to several centimeters depending upon the user's anatomy and desired degree of airflow restriction. Moreover, the member 222 may be extended in a ramped or incremented manner, for example, 5 mm increments over a specified period of time until the desired degree of projection is achieved. Alternatively and/or additionally, the member 222 may be moved cyclically in a manner corresponding to the respiratory cycle of the user. For instance, the member 222 may be maintained at an extension of 5 mm from the appliance 220 during inhalation but may be moved distally by an additional 5 mm or more during exhalation. This cycle may be repeated for a specified period of time or until treatment is concluded. Additionally, the device may be triggered on upon the sensing of sleep disordered breathing and then turned off once the sleep disordered breathing event has ceased, as described herein.

Figure 17A:
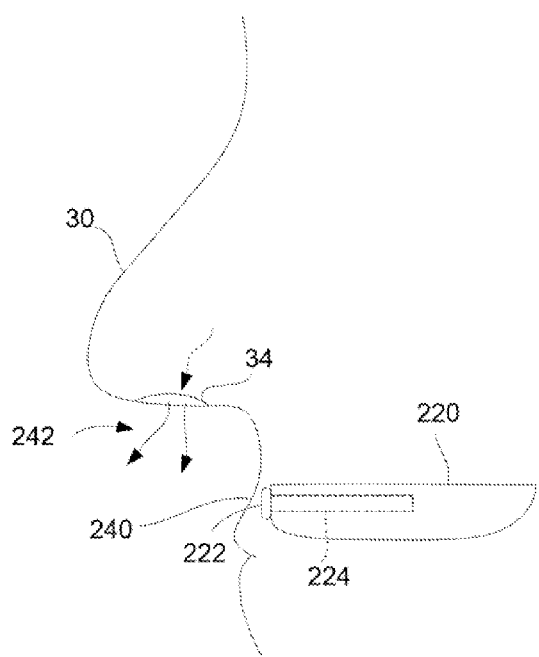
FIGS. 17A and 17B show an example of the device urging the patient's upper lip towards the nostrils for restricting the exhalation airflow.
Figure 17B:
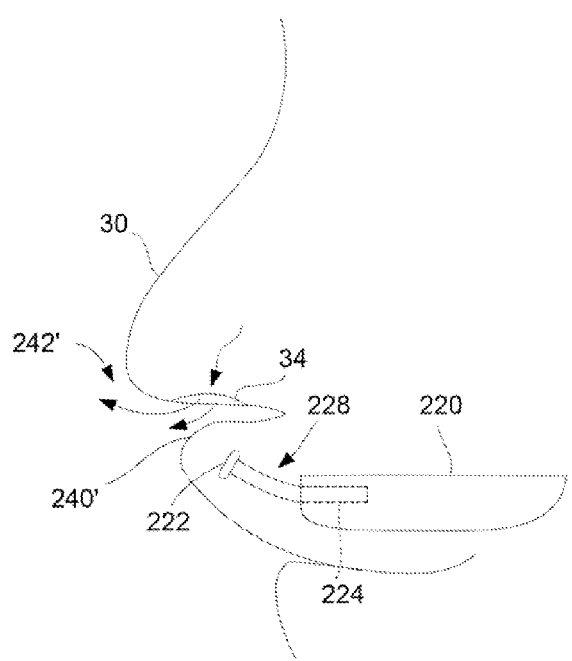

FIGS. 17A and 17B show an example of the device in use when positioned within the user's mouth. Prior to actuation, the oral appliance 220 may be seen secured against the patient's upper dentition with the member 222 resting posteriorly of the user's upper lip 240. Normal exhalation airflow 242 by the user is illustrated where the airflow exits through the nostrils 34. Upon the detection of sleep disordered breathing or after a preset period of time, the extendable member 222 may project from the oral appliance 220, as shown, to urge the patient's upper lip 240' towards the nostrils for restricting the exhalation airflow 242' from the nostrils 34. As described above, the positioning of the member 222 may be varied and/or may also be cyclically applied to correspond to the user's respiratory cycle.

While illustrative examples are described above, it will be apparent to one skilled in the art that various changes and modifications may be made therein. Moreover, various apparatus or methods described above are also intended to be utilized in combination with one another, as practicable. The appended claims are intended to cover all such changes and modifications that fall within the true spirit and scope of the invention.

What is claimed is:
1. An airflow restriction apparatus for restricting airflow from a subject, comprising:
    an oral appliance sized for placement upon or against a dentition of the subject;

a member movably attached to the appliance and positioned upon an anterior portion of the appliance such that the member is positionable posteriorly to an upper lip of the subject;

one or more supports attached to the member and slidably positioned within the appliance; and, one or more actuators positioned within or along the appliance and coupled to the member, wherein the member is reconfigurable between a low-profile configuration positioned against the appliance and an extended configuration positioned distal to the appliance when actuated by the one or more actuators.

2. The apparatus of claim 1 wherein the oral appliance is sized for placement along an upper dentition or ridge of the subject.

3. The apparatus of claim 1 wherein the one or more actuators comprise one or more motors.

4. The apparatus of claim 1 wherein the one or more supports comprise a curved or arcuate portion.

5. The apparatus of claim 1 further comprising a processor integrated within the appliance and in communication with the one or more actuators.

6. A method for restricting airflow from a nostril of a subject, comprising:

securing an oral appliance upon or against a dentition of the subject; and, urging an upper lip of the subject towards the nostril by distally extending a member attached to the appliance and positioned upon an anterior portion of the appliance by actuating one or more actuators to distally translate one or more su orts attached to the member such that the airflow from the nostril is restricted by the upper lip.

7. The method of claim 6 further comprising detecting a sleep disordered breathing event prior to urging.

8. The method of claim 6 wherein securing comprises positioning the oral appliance upon an upper dentition or ridge of the subject.

9. The method of claim 6 wherein urging comprises coordinating a movement of the member with a respiration cycle of the subject.

* * * * *